United States Patent
Struble et al.

(10) Patent No.: US 6,889,078 B2
(45) Date of Patent: May 3, 2005

(54) HYSTERESIS ACTIVATION OF ACCELERATED PACING

(75) Inventors: Chester L. Struble, Eijsden (NL); Pierre A. Grandjean, Warsage (BE)

(73) Assignee: Medtronic, Inc., Minneapolis, MN (US)

(*) Notice: Subject to any disclaimer, the term of this patent is extended or adjusted under 35 U.S.C. 154(b) by 360 days.

(21) Appl. No.: 09/842,233

(22) Filed: Apr. 26, 2001

(65) Prior Publication Data

US 2002/0183793 A1 Dec. 5, 2002

(51) Int. Cl.[7] ................................................ A61N 1/18
(52) U.S. Cl. ................................................... 607/9
(58) Field of Search ...................................... 607/9, 17

(56) References Cited

U.S. PATENT DOCUMENTS

| | | |
|---|---|---|
| 4,316,472 A | 2/1982 | Mirowski et al. |
| 4,375,817 A | 3/1983 | Engle |
| 4,379,459 A | 4/1983 | Stein |
| 4,384,585 A | 5/1983 | Zipes |
| 4,476,868 A | 10/1984 | Thompson et al. |
| 4,556,063 A | 12/1985 | Thompson et al. |
| 4,577,633 A | 3/1986 | Berkovits et al. |
| 4,587,970 A | 5/1986 | Holley et al. |
| 4,726,380 A | 2/1988 | Vollmann |
| 4,727,877 A | 3/1988 | Kallok |
| 4,800,883 A | 1/1989 | Winstrom |
| 4,821,723 A | 4/1989 | Baker et al. |
| 4,830,006 A | 5/1989 | Haluska |
| 4,880,005 A | 11/1989 | Pless et al. |
| 4,949,719 A | 8/1990 | Pless et al. |
| 4,953,551 A | 9/1990 | Mehra |
| 5,117,824 A | 6/1992 | Keimel |
| 5,131,388 A | 7/1992 | Pless et al. |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier |
| 5,269,298 A | 12/1993 | Adams et al. |
| 5,284,491 A | 2/1994 | Sutton et al. |
| 5,312,453 A | 5/1994 | Shelton et al. |
| 5,315,562 A | 5/1994 | Bradley et al. |
| 5,331,966 A | 7/1994 | Bennett et al. |
| 5,354,316 A | 10/1994 | Keimel |
| 5,501,701 A | 3/1996 | Markowitz et al. |
| 5,540,728 A | 7/1996 | Shelton et al. |
| 5,545,186 A | 8/1996 | Olson |
| 5,566,063 A | 10/1996 | Gerster et al. |
| 5,676,686 A | 10/1997 | Jensen et al. |
| 5,690,686 A | 11/1997 | Min et al. |

OTHER PUBLICATIONS

"Automatic Tachycardia Recognition" Arzbaecher et al. PACE, May–Jun. 1984 p. 541–547.

*Primary Examiner*—Mark Bockelman
(74) *Attorney, Agent, or Firm*—Paul H. McDowall; Girma Wolde-Michael

(57) ABSTRACT

An improved pacemaker has a hysteresis feature that activates accelerated pacing during periods of sinus arrest and/or extreme bradycardia. When the patient's intrinsic heart rate drops below a hysteresis rate, the pacemaker reverts to a programmable accelerated rate or to the average cardiac rate. Accelerated pacing is delivered for a programmable period of time, after which the pacing rate is gradually reduced toward a lower rate. If a desirable intrinsic rate is not attained after the pacing rate is reduced to the lower rate, the intervention cycle repeats.

36 Claims, 8 Drawing Sheets

HYSTERESIS ACTIVATION OF ACCELERATED PACING

FIELD OF THE INVENTION

The present invention relates to cardiac pacemakers, and more specifically to cardiac pacemakers that are responsive to reduced heart rate.

BACKGROUND

Sudden cardiac death is the main cause of death in heart failure patients and is believed to be associated with cardiac arrhythmias. Cardiac arrhythmias can be classified in two types: tachycardic and bradycardic. Tachycardic arrhythmias include ventricular tachycardia and ventricular fibrillation. Bradycardic arrhythmias include sinus arrest and extreme sinus bradycardia. Extreme bradycardic episodes can lead to extreme ischemic cardiac conditions and, as a result, enhanced myocardial sensitivity and possible propagation of cardiac arrhythmias.

To manage bradycardia, many pacemakers have a programmed lower pacing rate. If the patient's heart rate drops below this rate, the pacemaker intervenes by delivering pacing pulses at the lower pacing rate until the natural or intrinsic heart rate is restored to at least the lower pacing rate. Typically, this lower rate is programmed to a level well below the intrinsic rate of the sinus node frequency. For example, for patients with an intact sinus node function, the sinus rate is often programmed to 60 pulses per minute (ppm). Sleep rates may be programmed at an even slower rate, e.g., 50 ppm.

Some single chamber pacemakers incorporate a hysteresis feature that gives the heart an opportunity to beat on its own before the pacemaker intervenes by increasing the base pacing interval by the hysteresis interval. Hysteresis refers to extension of the range of cardiac rates at which stimulation pulses are inhibited. Dual chamber pacemakers, however, typically do not incorporate a hysteresis feature. As a result, patients using dual chamber pacemakers may receive unnecessary cardiac stimulation that potentially interferes with natural heart activity by preventing depolarization of the sinus node.

A heart failure patient often has an intrinsic atrial rhythm, but exhibits periods of sinus node dysfunction, including sinus arrest and/or extreme bradycardia. During periods of sinus node dysfunction, the patient receives backup pacing at the programmed lower rate. Because the paced rate is slower than a typical baseline heart rate, e.g., 75–90 beats per minute, cardiac output is significantly reduced. For example, assuming a paced rate of 60 pulses per minute, cardiac output is decreased by approximately 30% relative to the baseline heart rate. As a result, for heart failure patients, the programmed lower rate is insufficient for maintaining heart and body perfusion requirements.

Table 1 lists patents that disclose pacemakers that deliver pulses at an increased rate in response to a detected rapid drop in heart rate. After a timed period elapses, the pacing rate is decreased toward the lower pacing rate.

TABLE 1

| U.S. Pat. No. | Inventors | Title |
| --- | --- | --- |
| 5,284,491 | Sutton et al. | Cardiac Pacemaker with Hysteresis Behavior |
| 5,501,701 | Markowitz et al. | Pacemaker with Vasovagal Syncope Detection and Therapy |
| 5,540,728 | Shelton et al. | Pacemaker with Vasovagal Syncope Detection |
| 5,676,686 | Jensen et al. | Pacemaker with Vasovagal Syncope Detection |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to cardiac pacemakers in general, and responsiveness to sinus arrest and/or bradycardia in particular. These problems include, for example, delivery of stimulation pulses at a rate resulting in a lower cardiac output that is insufficient for maintaining heart and body perfusion requirements. Another problem associated with some known implementations of cardiac pacemakers is that the intrinsic rhythm may not be restored before the end of the intervention cycle. Various embodiments of the present invention have the object of solving at least one of the foregoing problems.

For example, it is an object of the present invention to provide sufficient cardiac stimulation to a patient to stimulate recovery of a normal intrinsic heart rhythm during a period of sinus arrest or extreme bradycardia.

In addition, it is object of the present invention to ensure that the intrinsic rhythm of the heart is restored before the cessation of cardiac intervention following a period of sinus arrest or extreme bradycardia.

Some embodiments of the invention include one or more of the following features: a hysteresis feature that activates accelerated pacing during periods of sinus arrest and/or extreme bradycardia; accelerated lower rate pacing for a prescribed duration; deceleration detection periods for detecting an intrinsic cardiac rhythm; and repeated intervention cycles when needed to provide additional cardiac stimulation. Hysteresis refers to extension of the range of cardiac rates at which stimulation pulses are inhibited. The hysteresis feature gives the heart an opportunity to beat on its own before the pacemaker intervenes by increasing the base pacing interval by the hysteresis interval. This feature is typically absent from dual chamber cardiac pacemakers. When a hysteresis interval times out, the pacemaker reverts to a programmable accelerated rate or to an average cardiac rate. Accelerated pacing is delivered for a programmable period of time, after which the pacing rate is gradually reduced toward a lower rate. If a desirable intrinsic rate is not attained after the pacing rate is reduced to the lower rate, the cycle repeats. Repeating the cycle when necessary ensures that the intrinsic heart rate is restored.

Various embodiments of the present invention may provide one or more of the following advantages: increased cardiac stimulation; increased cardiac output to a level sufficient to meet heart and body perfusion requirements; and improved detection of an intrinsic cardiac rhythm during the intervention cycle. For example, gradually decreasing the pacing rate from the accelerated rate to the programmed lower rate facilitates detection of an intrinsic cardiac rhythm during a cardiac recuperation phase, allowing intervention to cease, and normal heart activity to take over, if the intrinsic cardiac rhythm returns to normal before returning to the accelerated rate.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings, which form a part hereof, and in which are shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
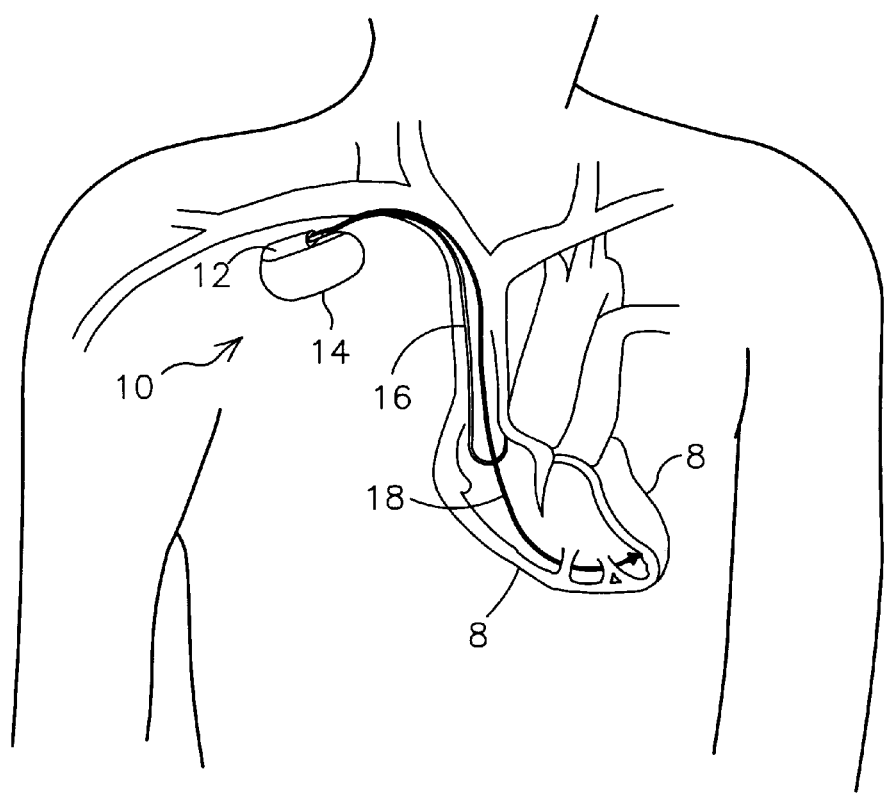
FIG. 1 is a simplified schematic view of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
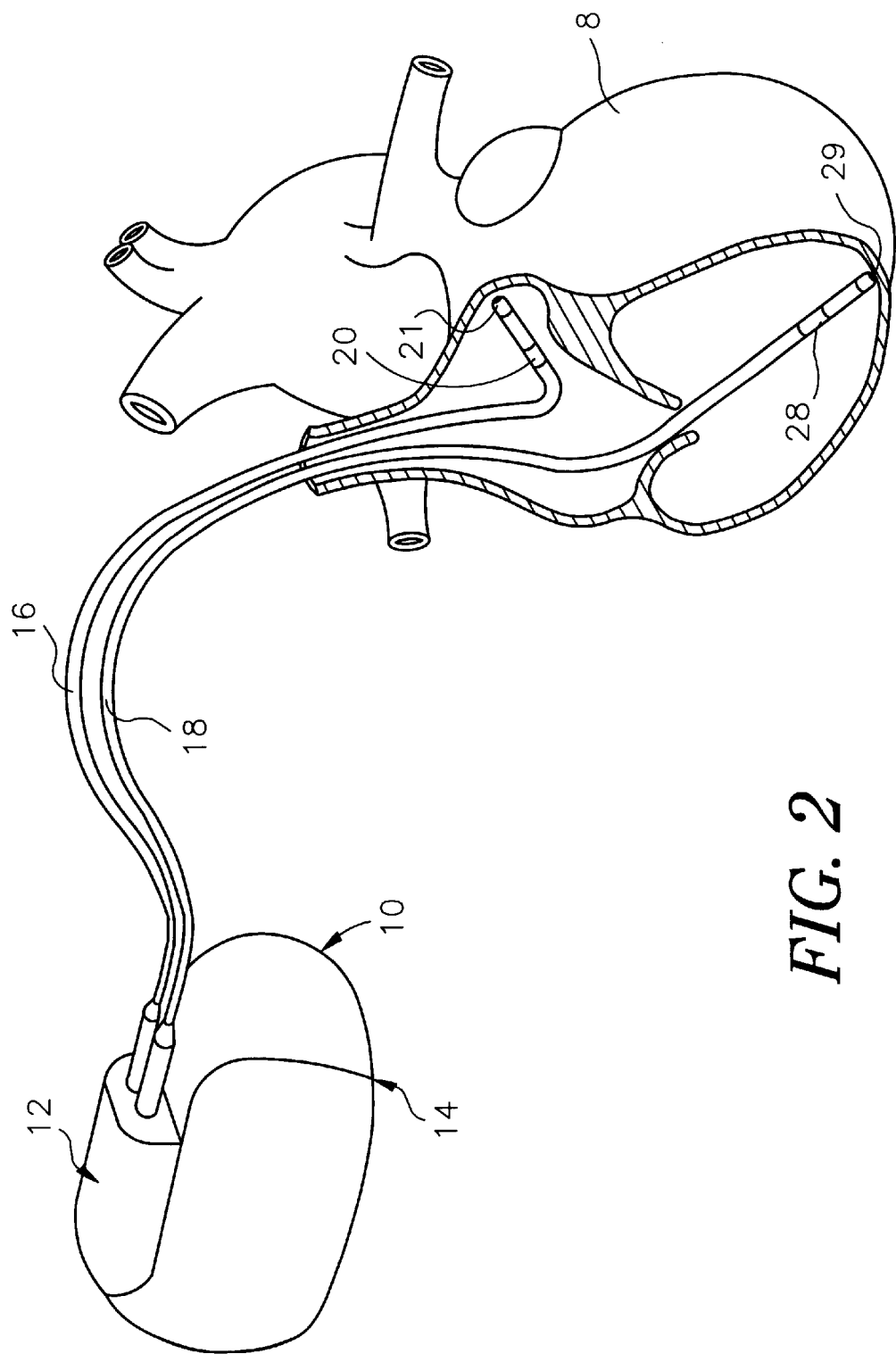
FIG. 2 shows a connector module and a hermetically sealed enclosure of the implantable medical device of FIG. 1 located near a human or mammalian heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
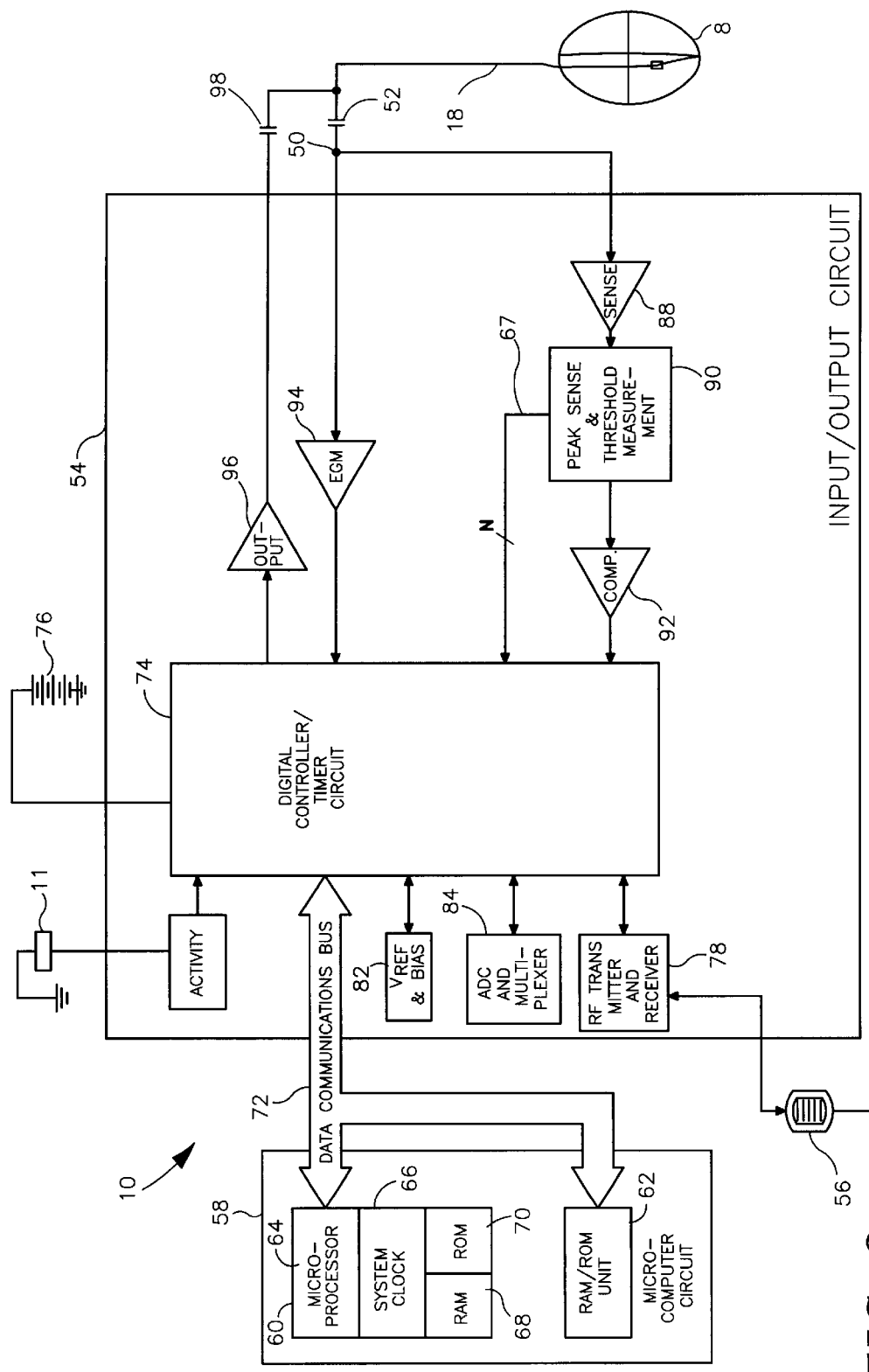
FIG. 3 shows a block diagram illustrating the constituent components of an implantable medical device having a microprocessor-based architecture.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head that transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/ downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
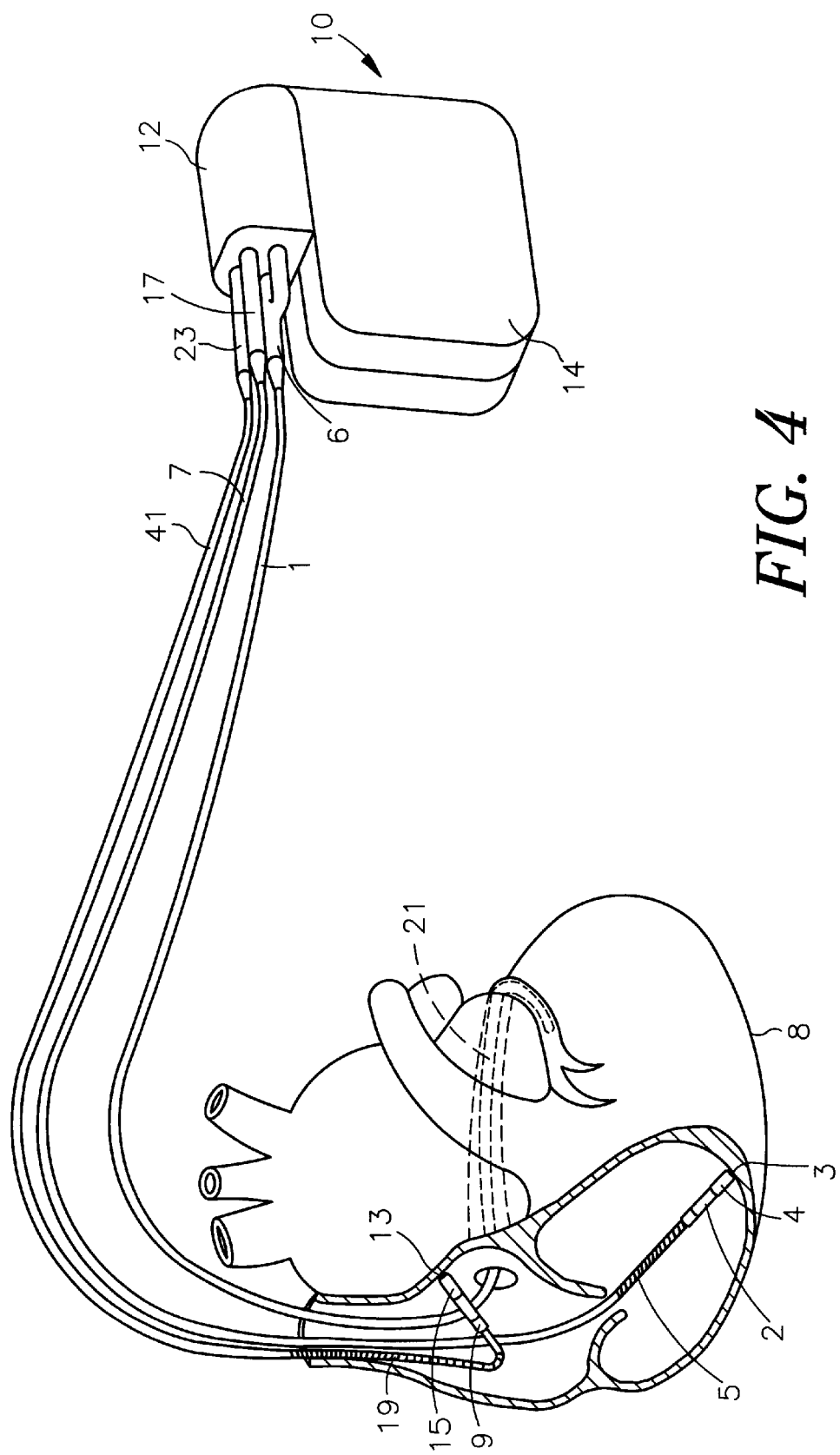
FIG. 4 illustrates an implantable medical device and a corresponding lead set.
Figure 5:
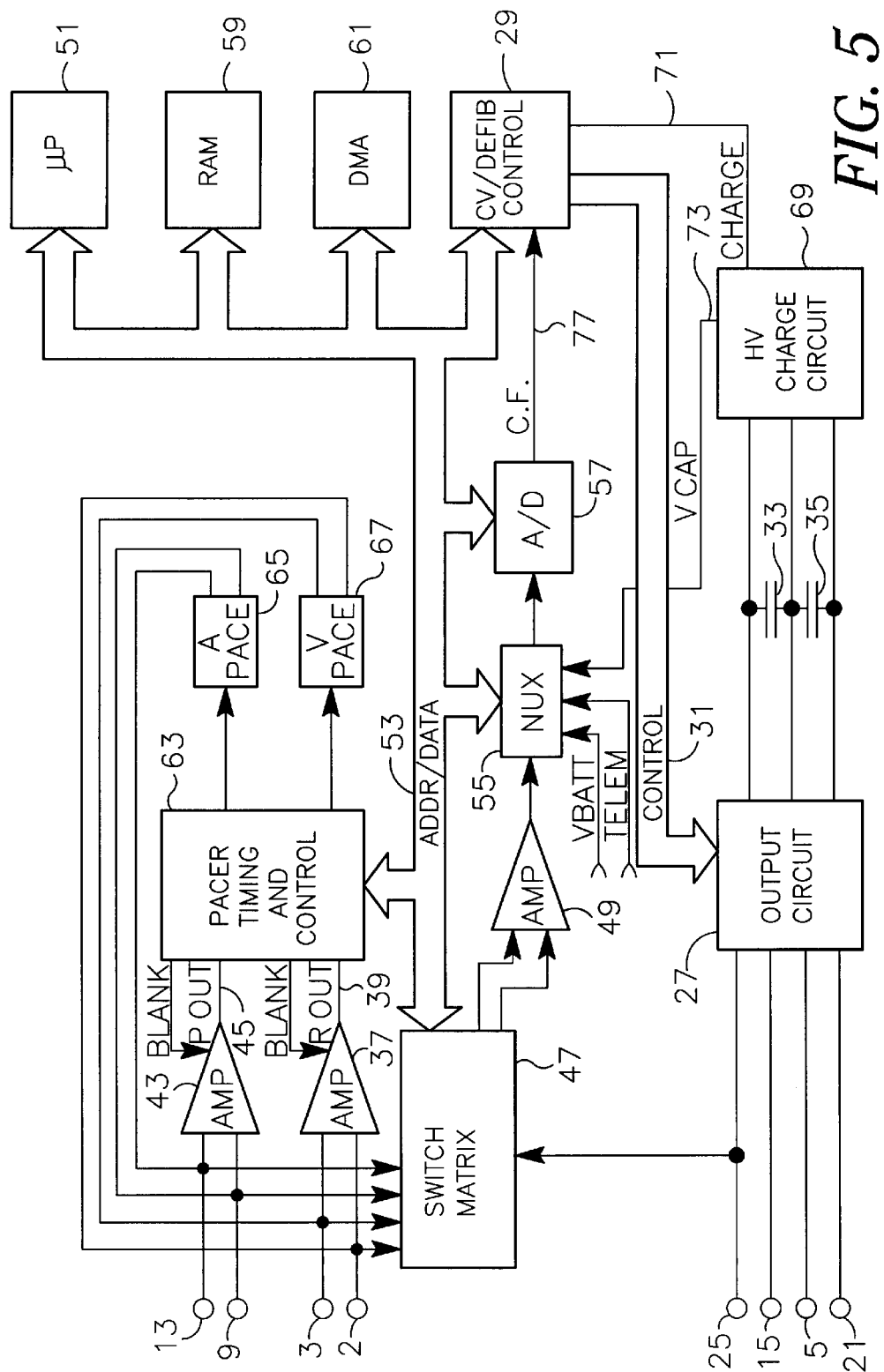
FIG. 5 is a functional schematic diagram of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P–R intervals and R–P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling the generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches that control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry that may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Before proceeding with a more detailed explanation of the invention, it is helpful to review the following definitions:

The "intrinsic rhythm" or "intrinsic rate" of the heart is the rate at which the heart naturally beats on its own, without stimulation by a pacemaker-provided stimulus.

"Pacing rate" refers to the rate at which stimulation pulses are provided to the heart from the pacemaker.

The "lower pacing rate" or "lower rate" of the pacemaker is the minimum rate at which the pacemaker will provide stimulation pulses. In patients having intact sinus node function, the lower rate is typically programmed at approximately 60 pulses per minute (ppm).

The "upper pacing rate" or "upper rate" of the pacemaker is the maximum rate at which the pacemaker will deliver stimulation pulses.

"Hysteresis" refers to extension of the range of rates at which inhibition of the pacemaker pulses will occur. The base pacing interval is increased by the hysteresis interval. Thus, hysteresis provides a longer escape interval, thereby giving the heart an opportunity to beat on its own before the pacemaker provides stimulation pulses. The hysteresis rate can be programmed at any level below the programmed lower rate of the pacemaker. For example, if the programmed lower rate is 60 ppm, the hysteresis rate might be programmed at 55, 50, 45, 40, 35, or 30 beats per minute (bpm). In a specific implementation, the difference between the hysteresis rate and the programmed lower rate is an integral multiple of 10 bpm, e.g., 50, 40, or 30 bpm.

Figure 6:
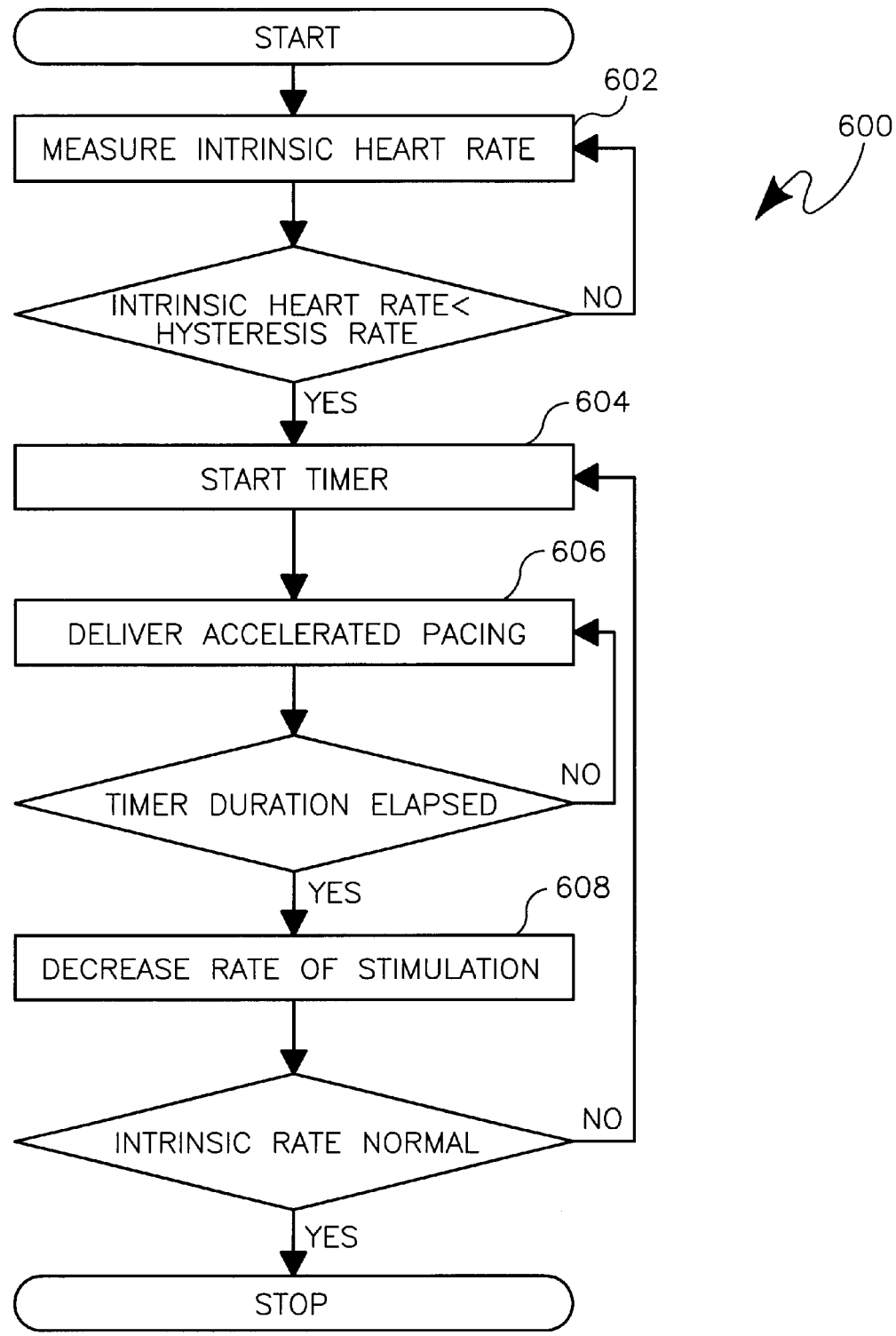
FIG. 6 is a flow diagram depicting an example mode of operation of an implantable medical device according to one embodiment of the present invention.

FIG. 6 shows an example mode of operation 600 of IMD 10, according to an example embodiment of the invention. First, IMD 10 measures the intrinsic rate of the heart (602). If the intrinsic rate is greater than or equal to the hysteresis rate, IMD 10 does not intervene. If, on the other hand, the intrinsic rate decreases below the hysteresis rate, IMD 10 detects the onset of sinus arrest or extreme bradycardia. In response to this bradycardic insult, IMD 10 starts a timer (604) and begins delivering stimulation pulses at an accelerated rate greater than the programmed lower rate of IMD 10 (606). The timer facilitates limiting the duration of the accelerated pacing to, for example, 20 seconds. IMD 10 delivers the stimulation pulses either at a programmable accelerated rate or at the average cardiac rate over a period immediately preceding the bradycardic insult, e.g., the past minute. The average cardiac rate for the patient can be sensed and stored within IMD 10. In one embodiment, IMD 10 delivers the stimulation pulses at the greater of the programmable accelerated rate and the average cardiac rate.

After the timer's duration elapses, IMD 10 decreases the rate of stimulation pulses at a programmable deceleration rate of, for example, 5% per second, toward the programmed lower rate of IMD 10 (608). Decelerating the rate of delivery of stimulation pulses allows IMD 10 to detect recovery of an intrinsic cardiac rhythm during a cardiac recuperation phase. If a normal intrinsic rate is not attained by the end of this deceleration period, IMD 10 reverts to the accelerated lower rate (606), and the cycle repeats. Intervention ends when the intrinsic rate returns to a normal rate or when a ventricular rhythm exceeds the pacing rate, whichever is greater. If, at a later time, the intrinsic rate decreases below the hysteresis rate again, IMD 10 begins the intervention cycle again.

Figure 7:
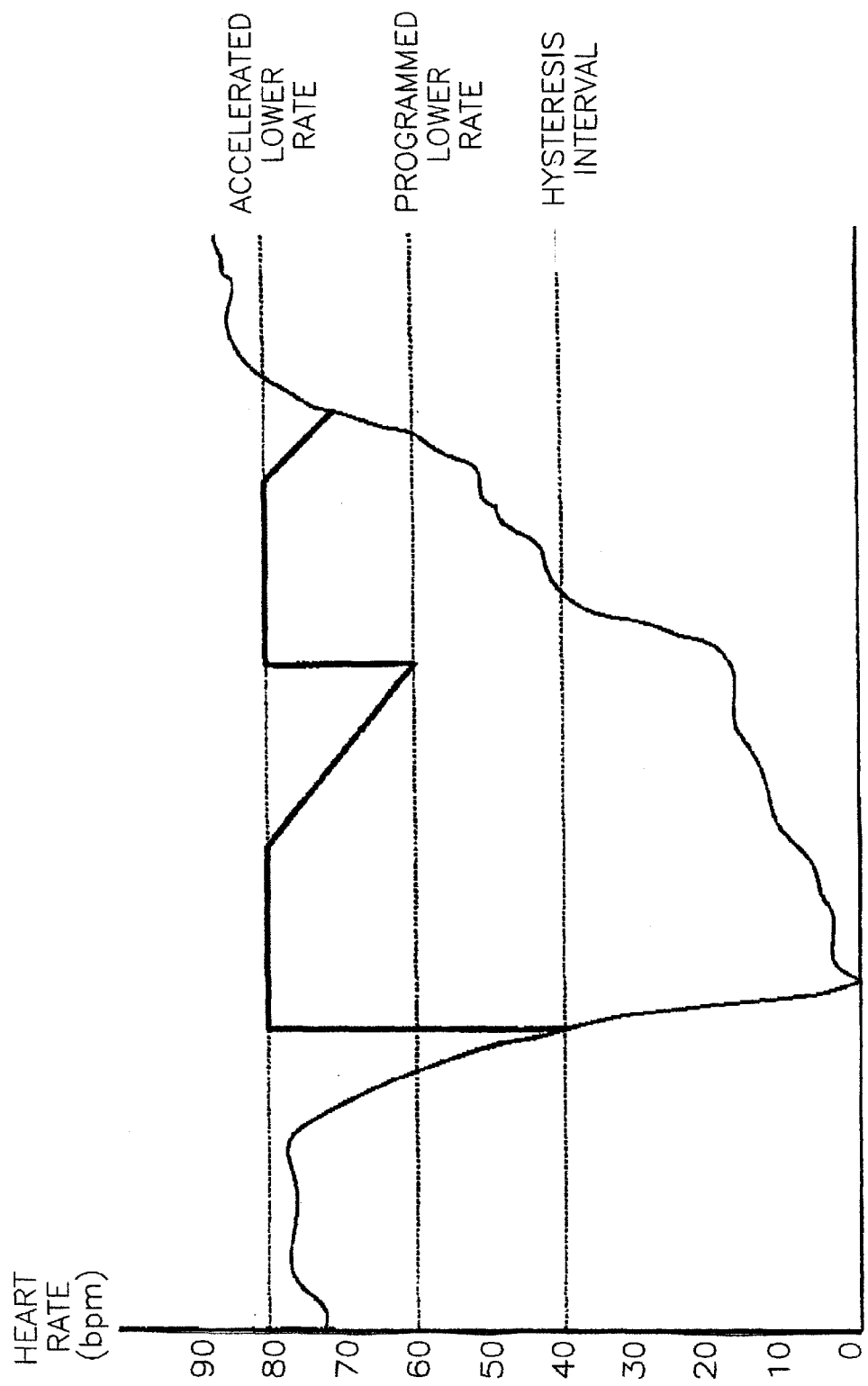
FIG. 7 illustrates an operational example of the mode of operation of FIG. 6.

FIG. 7 shows an operational example of mode of operation 600 of IMD 10 in which IMD 10 delivers stimulation pulses at a programmable accelerated rate of 80 beats per minute (bpm). As shown in FIG. 7, before sinus arrest, the patient has an average heart rate of approximately 75 bpm. The patient then enters sinus arrest, with the heart rate decreasing sharply to zero. When the heart rate decreases below the hysteresis rate of 40 bpm, IMD 10 intervenes by starting a timer (604) and starting delivery of accelerated pacing (606). In this operational example, the programmed accelerated lower rate of 80 ppm is faster than the pre-sinus arrest average cardiac rate of 75 bpm. Accordingly, IMD 10 delivers stimulation pulses at the programmed accelerated lower rate, 80 ppm. IMD 10 delivers accelerated pacing for a period of, for example, 20 seconds, and then gradually decreases the rate of stimulation toward the programmed lower rate, 60 bpm in this example, at a programmed rate of deceleration (608).

In this operational example, the rate of deceleration is programmed at 5% of the difference between the accelerated lower rate (80 ppm=750 ms) and the programmed lower rate (60 ppm=1000 ms)), i.e., 1 ppm per second. This represents a deceleration rate of approximately 12.5 ms per second (1000 ms–750 ms=250 ms×5%=12.5 ms). When the rate of stimulation is decreased to the programmed lower rate, IMD 10 determines that normal sinus activity has not yet been restored, as the cardiac rate is still considerably less than the hysteresis rate. IMD 10 therefore repeats the intervention cycle (604). The cardiac rate exceeds the pacing rate during the deceleration phase of the second intervention cycle, and IMD 10 stops delivery of stimulation pulses.

Figure 8:
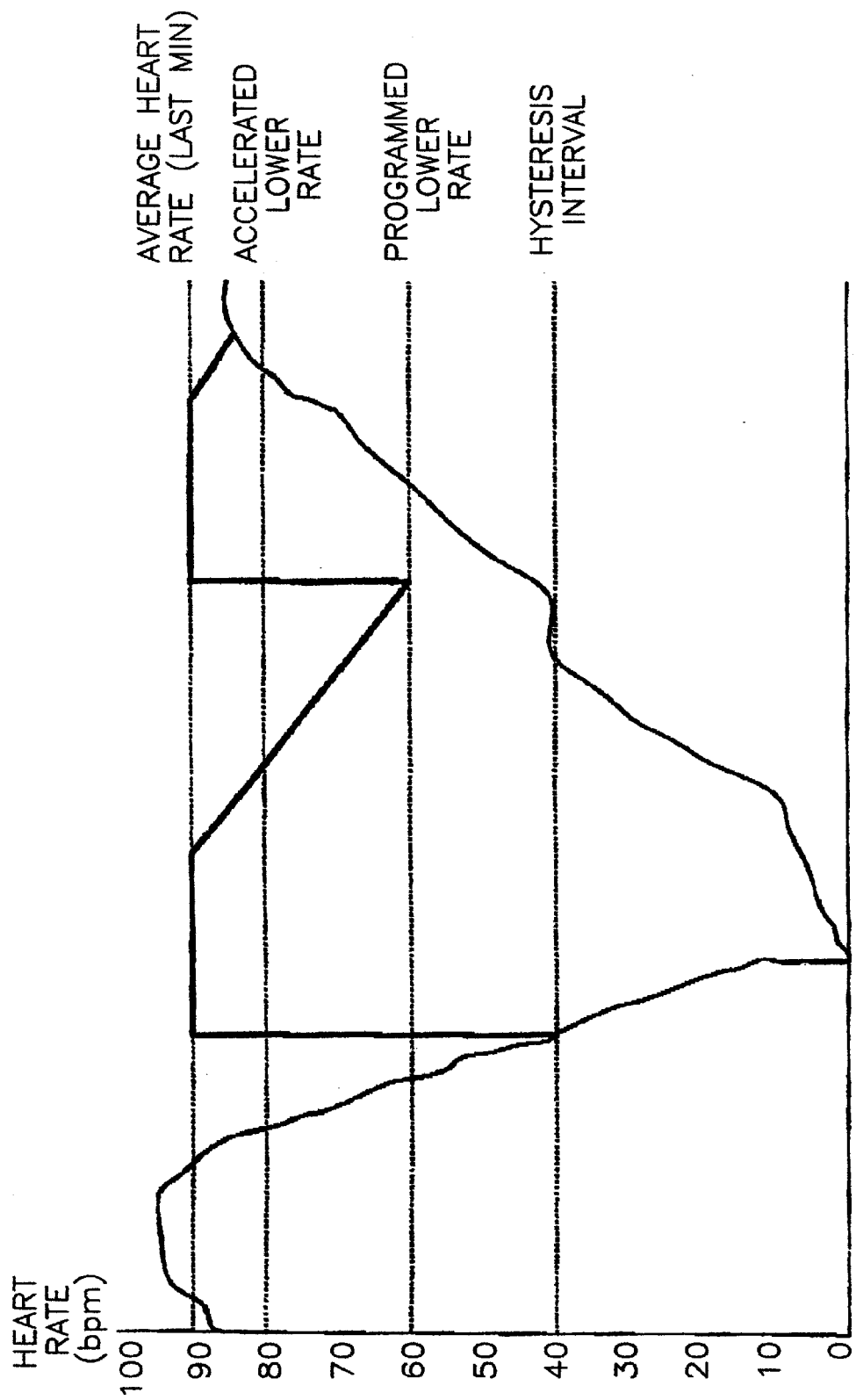
FIG. 8 illustrates another operational example of the mode of operation shown in FIG. 6.

FIG. 8 shows another operational example of mode of operation 600 of IMD 10 in which IMD 10 delivers stimulation pulses at the average cardiac rate over the past minute, 90 bpm in this example. In FIG. 8, before sinus arrest, the patient has an average heart rate of approximately 90 bpm. The patient then enters sinus arrest, with the heart rate decreasing sharply to zero. When the heart rate decreases below the hysteresis rate of 40 bpm, IMD 10 intervenes by starting a timer (604) and starting delivery of accelerated pacing (606). In this operational example, the programmed accelerated lower rate of 80 ppm is slower than the average cardiac rate before sinus arrest of 90 bpm. Accordingly, IMD 10 delivers stimulation pulses at the average cardiac rate, 90 ppm.

IMD 10 delivers accelerated pacing for a period of, for example, 20 seconds, and then gradually decreases the rate of stimulation toward the programmed lower rate, 60 ppm in this example (608). In the operational example of FIG. 8, the rate of deceleration is programmed at 1 ppm per second. When the rate of stimulation is decreased to the programmed lower rate, IMD 10 determines that normal sinus activity has not yet been restored, as the cardiac rate is still well below the hysteresis rate. IMD 10 therefore repeats the intervention cycle (604). During the deceleration phase of the second intervention cycle, IMD 10 stops delivering stimulation pulses, as the cardiac rate exceeds the pacing rate.

By delivering accelerated pacing at a rate higher than the programmed lower rate, IMD 10 provides greater cardiac stimulation to a heart failure patient who exhibits periods of sinus node dysfunction. Pacing is delivered at a rate sufficient to satisfy heart and body perfusion requirements.

The preceding specific embodiments are illustrative of the practice of the invention. It is to be understood, therefore, that other expedients known to those skilled in the art or disclosed herein may be employed without departing from the invention or the scope of the claims. For example, the present invention is not limited to applications in which the various rates are programmed to the particular values described above. Moreover, those of skill in the art will appreciate that the invention can be made an integral part of single chamber and dual chamber pacemakers that operate in one or more of the programmed modes: AAI, AAIR, VVI, VVIR, DDD, DDDR, VVI-ICD, VVIR-ICD, DDD-ICD, and/or DDDR-ICD. The present invention is also not limited to the treatment of sinus arrest and/or extreme bradycardia per se, but may find further application for facilitating post shock therapy for tachycardic arrhythmias by increasing the basic backup pacing rate immediately following defibrillation. The present invention further includes in its scope methods of making and using the implantable medical devices described hereinabove. These applications, as well as other modifications, are contemplated within the scope and spirit of the specification, drawings, abstract, and the claims that follow.

In the claims, means-plus-functions claims are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device compromising:
   a sensing arrangement to sense electrical cardiac signals;
   a pulse generator to deliver stimulation pulses to a heart; and
   a control arrangement, responsive to the sensing arrangement, to respond to an intrinsic heart rate decreasing below a first hysteresis rate by directing the pulse generator to deliver stimulation pulses at an accelerated rate greater than a programmed lower rate for a programmed duration, decreasing the rate of delivery after the proqrammed duration, and directing the pulse generator to deliver additional stimulation pulses at the accelerated rate if the intrinsic heart rate does not increase to a level at or above the first rate, wherein the control arrangement is further configured to select the accelerated rate as the greater of a fixed rate and art average heart rate over a period immediately before decrease of the intrinsic heart rate below the hysteresis rate.

2. The implantable medical device of claim 1, wherein the control arrangement is further configured to direct the pulse generator to repeat delivering additional stimulation pulses at the accelerated rate and decreasing the rate of delivery until the intrinsic heart rate increases to a level at or above the hysteresis rate.

3. The implantable medical device of claim 1, wherein the accelerated rate is programmed to a fixed rate greater than the programmed lower rate.

4. The implantable medical device of claim 1, wherein the accelerated rate is an average heart rate over a period immediately before decrease of the intrinsic heart rate below the hysteresis rate.

5. The implantable medical device of claim 1, wherein the control arrangement is further configured to decrease the rate of delivery of the stimulation pulses toward the programmed lower rate at a programmed rate of deceleration.

6. The implantable medical device of claim 1, wherein the control arrangement is further configured to determine the programmed rate of deceleration as a function of a percentage of a difference between the accelerated rate and the programmed lower rate.

7. The implantable medical device of claim 1, wherein the control arrangement is further configured to direct the pulse generator to cease delivery of stimulation pulses when the intrinsic heart rate returns to a normal rate.

8. The implantable medical device of claim 1, wherein the control arrangement is further configured to direct the pulse generator to cease delivery of stimulation pulses when a ventricular rhythm exceeds the rate of delivery of stimulation pulses.

9. The implantable medical device of claim 1, wherein the implantable medical device is a single-chamber cardiac pacemaker configured to operate in at least one of the group of modes consisting of AAI, AAIR, VVI, VVIR, VVI-ICD, and VVIR-ICD operational modes.

10. The implantable medical device of claim 1, wherein the implantable medical device is a dual-chamber cardiac pacemaker configured to operate in at least one of the group of modes consisting of AAI, AAIR, VVI, VVIR, DDD, DDDR, VVI-ICD, VVIR-ICD,DDD-ICD, and DDDR-ICD operational modes.

11. The implantable medical device of claim 1, further comprising means for repeating delivering additional stimulation pulses at the accelerated rate and decreasing the rate of delivery until the intrinsic heart rate increases to a level at or above the hysteresis rate.

12. The implantable medical device of claim 1, further comprising means for programming the implantable medical device.

13. An implantable medical device system comprising:
    a sensing arrangement to sense electrical cardiac signals;
    a pulse generator to deliver stimulation pulses to a heart;
    at least one pacing lead, coupled to the pulse generator and configured to deliver the stimulation pulses to a chamber of the heart; and
    a control arrangement responsive to the sensing arrangement and configured to respond to an intrinsic heart rate decreasing below a hysteresis rate by directing the pulse generator to deliver stimulation pulses to the heart at an accelerated rate greater than a programmed lower rate for a programmed duration, decreasing the rate of delivery after the programmed duration, and repeating directing the pulse generator to deliver stimulation pulses at the accelerated rate unless the intrinsic heart rate is recovered, wherein the control arrangement is further configured to select the accelerated rate as the greater of a fixed rate and an average heart rate over a period immediately before decrease of the intrinsic heart rate below the hysteresis rate.

14. The implantable medical device system of claim 13, wherein the accelerated rate is programmed to a fixed rate greater than the programmed lower rate.

15. The implantable medical device system of claim 13, wherein the accelerated rate is an average heart rate over a period immediately before decrease of the intrinsic heart rate below the hysteresis rate.

16. The implantable medical device system of claim 13, wherein the control arrangement is further configured to decrease the rate of delivery toward the programmed lower rate at a programmed rate of deceleration.

17. The implantable medical device system of claim 16, wherein the control arrangement is further configured to determine the programmed rate of deceleration as a function of a percentage of a difference between the accelerated rate and the programmed lower rate.

18. The implantable medical device system of claim 13, wherein the control arrangement is further configured to direct the pulse generator to cease delivery of stimulation pulses when the intrinsic heart rate returns to a normal rate.

19. The implantable medical device system of claim 13, wherein the control arrangement is further configured to direct the pulse generator to cease delivery of stimulation pulses when a ventricular rhythm exceeds the rate of delivery of stimulation pulses.

20. The implantable medical device system of claim 13, wherein the implantable medical device system comprises a single-chamber cardiac pacemaker configured to operate in at least one of the group of modes consisting of AAI, AAIR, VVI, VVIR, VVI-ICD, and VVIR-ICD operational modes.

21. The implantable medical device system of claim 13, wherein the implantable medical device system comprises a dual-chamber cardiac pacemaker configured to operate in at least one of the group of modes consisting of AAI, AAIR, VVI, VVIR, DDD, DDDR, VVI-ICD, VVIR-ICD, DDD-ICD, and DDDR-ICD operational modes.

22. The implantable medical device system of claim 13, further comprising a programming arrangement to program the control arrangement.

23. The implantable medical device system of claim 22, wherein the programming arrangement comprises a microprocessor to provide an encoded signal to the control arrangement.

24. A method of cardiac pacing comprising:

detecting an intrinsic heart rate;

when the intrinsic heart rate decreases below a hysteresis rate, delivering stimulation pulses to a heart at an accelerated rate greater than a programmed lower rate for a programmed duration;

decreasing the rate of delivery after the programmed duration; and repeating delivering stimulation pulses at the accelerated rate unless the intrinsic heart rate is recovered, further comprising selecting the accelerated rate as the greater of a fixed rate and an average heart rate over a period immediately before decrease of the intrinsic heart rate below the hysteresis rate.

25. The method of cardiac pacing of claim 24, wherein the accelerated rate is programmed to a fixed rate greater than the programmed lower rate.

26. The method of cardiac pacing of claim 24, wherein the accelerated rate is an average heart rate over a period immediately before decrease of the intrinsic heart rate below the hysteresis rate.

27. The method of cardiac pacing of claim 24, further comprising decreasing the rate of delivery toward the programmed lower rate at a programmed rate of deceleration.

28. The method of cardiac pacing of claim 27, further comprising determining the programmed rate of deceleration as a function of a percentage of a difference between the accelerated rate and the programmed lower rate.

29. The method of cardiac pacing of claim 24, further comprising ceasing delivery of stimulation pulses when the intrinsic heart rate returns to a normal rate.

30. The method of cardiac pacing of claim 24, further comprising ceasing delivery of stimulation pulses when a ventricular rhythm exceeds the rate of delivery of stimulation pulses.

31. A method of cardiac pacing comprising:

defining a hysteresis rate lower than a programmed lower rate and an accelerated rate greater than the programmed lower rate;

when an intrinsic heart rate decreases below the hysteresis rate, delivering stimulation pulses to a heart at the accelerated rate for a programmed duration;

decreasing the rate of delivery after the programmed duration at a programmed rate of deceleration; and ceasing delivery of stimulation pulses when the intrinsic heart rate returns to a normal rate, further comprising selecting the accelerated rate as the greater of a fixed rate and an average heart rate over a period immediately before decrease of the intrinsic heart rate below the hysteresis rate.

32. A method of manufacturing an implantable medical device comprising:

providing a sensing arrangement to sense electrical cardiac signals;

providing a pulse generator to deliver stimulation pulses to a heart;

coupling a control arrangement to the sensing arrangement; and programming the control arrangement to respond to an intrinsic heart rate decreasing below a hysteresis rate by directing the pulse generator to deliver stimulation pulses to the heart at an accelerated rate greater than a programmed lower rate for a programmed duration decreasing the rate of delivery after the programmed duration, and repeating directing the pulse generator to deliver stimulation pulses at the accelerated rate unless the intrinsic heart rate is recovered, further comprising programming the control arrangement to select the accelerated rate as the greater of a fixed rate and an average heart rate over a period immediately before decrease of the intrinsic heart rate below the hysteresis rate.

33. The method of manufacturing an implantable medical device of claim 32, further comprising programming the control arrangement to decrease the rate of delivery toward the programmed lower rate at a programmed rate of deceleration.

34. The method of manufacturing an implantable medical device of claim 32, further comprising programming the control arrangement to direct the pulse generator to cease delivery of stimulation pulses when the intrinsic heart rate returns to a normal rate.

35. The method of manufacturing an implantable medical device of claim 32, further comprising programming the control arrangement to direct the pulse generator to cease delivery of stimulation pulses when a ventricular rhythm exceeds the rate of delivery of stimulation pulses.

36. The method of manufacturing an implantable medical device of claim 32, further comprising configuring the implantable medical device to operate in at least one of the group of modes consisting of AAI, AAIR, VVI, VVIR, DDD, DDDR, VVI-ICD, VVIR-ICD, DDD-ICD, and DDDR-ICD operational modes.

* * * * *